(12) United States Patent
Solanki et al.

(10) Patent No.: US 8,058,302 B2
(45) Date of Patent: Nov. 15, 2011

(54) PROCESS FOR PREPARING PURE ANASTROZOLE

(75) Inventors: Kirtipalsinh Sajjansinh Solanki, Gujarat (IN); Manoj Kumar Singh, Ahmedabad (IN); Jay Shantilal Kothari, Ahmedabad (IN); Virendra Kumar Agarwal, Ahmedabad (IN)

(73) Assignee: Cadila Healthcare Limited, Ahmedabad, Gujarat (IN)

( * ) Notice: Subject to any disclaimer, the term of this patent is extended or adjusted under 35 U.S.C. 154(b) by 93 days.

(21) Appl. No.: 12/303,235

(22) PCT Filed: Sep. 4, 2006

(86) PCT No.: PCT/IN2006/000338
§ 371 (c)(1),
(2), (4) Date: Jan. 20, 2009

(87) PCT Pub. No.: WO2007/141799
PCT Pub. Date: Dec. 13, 2007

(65) Prior Publication Data
US 2009/0247765 A1    Oct. 1, 2009

(30) Foreign Application Priority Data
Jun. 5, 2006 (IN) .......................... 865-MUM-2006

(51) Int. Cl.
*A61K 31/41* (2006.01)
*C07D 249/00* (2006.01)

(52) U.S. Cl. ..................................... 514/383; 548/262.2
(58) Field of Classification Search ................... 514/383; 548/262.2
See application file for complete search history.

(56) References Cited

U.S. PATENT DOCUMENTS

| | | | |
|---|---|---|---|
| 4,935,437 A * | 6/1990 | Edwards et al. | 514/383 |
| 2006/0035950 A1 | 2/2006 | Alnabari | |
| 2006/0189670 A1 | 8/2006 | Khile | |
| 2006/0276657 A1 | 12/2006 | Villa et al. | |

FOREIGN PATENT DOCUMENTS

| | | |
|---|---|---|
| EP | 0296749 A1 | 12/1988 |
| WO | WO-2005105762 A | 11/2005 |
| WO | WO-2006108155 A | 10/2006 |
| WO | WO-2007002720 A | 1/2007 |

OTHER PUBLICATIONS

Tang, Gu-Ping et al, "2-A3-(2-Cyano-2-Propyl)-5-...", Structure Reports Online, Acta Cryst., 2005, 02330-02331, vol. E61, No. 8, International Union of Crystallography.

* cited by examiner

*Primary Examiner* — Susannah Chung
(74) *Attorney, Agent, or Firm* — IpHorgan Ltd.

(57) ABSTRACT

The present invention discloses two new related substances (6) and (7) of Anastrozole synthesis from Q.A. Salt (5) as in Scheme—1 and purification procedures to get Anastrozole (1) free from (6) and (7).

13 Claims, No Drawings

PROCESS FOR PREPARING PURE ANASTROZOLE

FIELD OF INVENTION

Aromatase is an enzyme, which effects aromatisation of ring A in the metabolic formation of various steroid hormones. Various cancers, for example, breast cancer are dependent upon circulating steroid hormones, which have an aromatic ring A. Such cancers can be treated by removing the source of ring A aromatised steroid hormones, for example, by the combination of oophorectomy and adrenalectomy. An alternative way of obtaining the same effect is by administering a chemical compound, which inhibits the aromatisation of the steroid ring A.

Anastrozole is a non-steroidal antineoplastic, claimed to inhibit the aromatase (oestrogen synthase) activity. It is useful in the treatment of advanced breast cancer in postmenopausal women.

BACKGROUND OF INVENTION

Synthesis of Anastrozole is reported in U.S. Pat. No. 4,935,437 and European Patent Application EP 0,296,749. The synthetic route mentioned in the said patents suffers a major disadvantage of the formation of Anastrozole regioisomer (2).

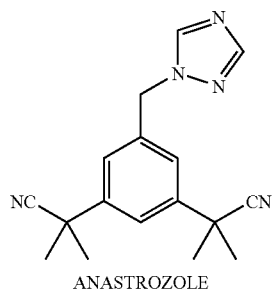

ANASTROZOLE (1)

ANASTROZOLE REGIOISOMER (2)

To overcome the formation of regioisomer (2), another synthetic route is reported in U.S. Pat. No. 4,935,437; in which compound (3) is reacted with 4-amino-1,2,4-triazole (4) to form quaternary ammonium salt (5), which further undergoes diazotisation reaction to give Anastrozole (1) free from regioisomeric impurity (2) (Scheme—1).

SCHEME-1

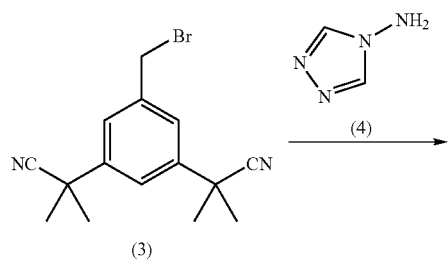

(3)

(4)

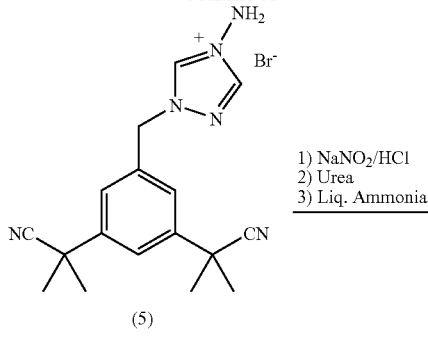

(5)
Q. A.-Salt

1) NaNO$_2$/HCl
2) Urea
3) Liq. Ammonia

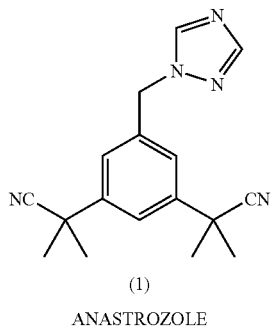

(1)
ANASTROZOLE

It has been observed that the cyano groups undergo hydrolysis in various conditions to form hydrolysed related compounds.

OBJECTS OF THE INVENTION

It is an object of the present invention to provide an improved process for the preparation of pure Anastrozole (1) free from impurities arising due to hydrolysis of cyano groups during the course of the preparation of Anastrozole (1).

DESCRIPTION OF INVENTION

Intermediate (3) undergoes condensation with 4-amino-1,2,4-triazole (4) in a suitable solvent to give 4-amino-1-[3,5-bis-(1-cyano-1-methylethyl)benzyl]-1H-[1,2,4]triazolium bromide (Q.A.-salt) (5) in good yield.

It has been further observed that during the preparation of Anastrozole, hydrolysis of cyano groups also takes place leading to the formation of two major related substances. The hydrolysis products formed due to hydrolysis are characterized as 2-[3-(cyanodimethyl-methyl)-5-[1,2,4]triazol-1-ylmethyl-phenyl]-isobutyramide (6) and 2-[3-(1-carbamoyl-1-methylethyl)-5-[1,2,4]triazol-1-ylmethylphenyl]-isobutyramide (7). Both the substances are isolated and well characterized by using NMR and mass analysis. The $^1$H-NMR, $^{13}$C-NMR and mass analysis of the isolated products 2-[3-(cyanodimethyl-methyl)-5-[1,2,4]triazol-1-ylmethyl-phenyl]-isobutyramide (6) and 2-[3-(1-carbamoyl-1-methylethyl)-5-[1,2,4]triazol-1-ylmethylphenyl]-isobutyramide (7) are in accordance with the chemical structure. $^1$H-NMR of compound (6) shows three singlets at δ 7.4, 7.3 and 7.24 for three protons in aromatic ring, and two protons at δ 6.95 for amide group. However four methyl groups appear at δ 1.65 and 1.41, each for six protons. The $^{13}$C-NMR of compound (6) shows a quaternary peak at δ 177.4 for amide carbonyl carbon, three tertiary aromatic carbons at δ 125.0, 122.7 and 122.2; two aliphatic quaternary carbons at δ 52.1 and 46.1 and two peaks for methyl carbons at δ 28.4 and 26.7. Further, the structure is also confirmed by the mass analysis of compound (6).

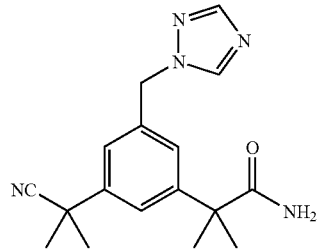

(6)

2-[3-(Cyano-dimethyl-methyl)-5-[1,2,4]triazol-1-ylmethyl-phenyl]-isobutyramide

The 1H-NMR of compound (7) shows peaks at δ 6.86 for amide protons and its 13C-NMR shows amide carbonyl carbon at δ 179.6. Further, the structure is also confirmed by the mass analysis of compound (7).

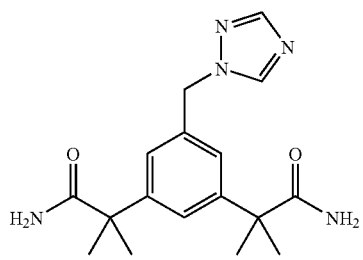

(7)

2-[3-(1-Carbamoyl-1-methylethyl)-5-[1,2,4]triazol-1-ylmethylphenyl]-isobutyramide The HPLC chromatogram of Anastrozole shows presence of related substances (6) and (7) in 0.02% to 1.0% in crude product which are removed by the repeated crystallization using an alcoholic solvent with a mixture of hydrocarbon as anti-solvent.

The removal of the related substances 2-[3-(cyanodimethyl-methyl)-5-[1,2,4]triazol-1-ylmethyl-phenyl]-isobutyramide (6) and 2-[3-(1-carbamoyl-1-methylethyl)-5-[1,2,4]triazol-1-ylmethylphenyl]-isobutyramide (7) are accomplished by the crystallization method using various solvent systems to get Anastrozole in its purer form. Thus, the main embodiment of the present invention relates to the products 2-[3-(cyanodimethyl-methyl)-5-[1,2,4]triazol-1-ylmethyl-phenyl]-isobutyramide (6) and 2-[3-(1-carbamoyl-1-methylethyl)-5-[1,2,4]triazol-1-ylmethylphenyl]-isobutyramide (7) as related substances in Anastrozole. According to another embodiment, the present invention also relates to the process for the preparation of Anastrozole with related substances 2-[3-(cyanodimethyl-methyl)-5-[1,2,4]triazol-1-ylmethyl-phenyl]-isobutyramide (6) and 2-[3-(1-carbamoyl-1-methylethyl)-5-[1,2,4]triazol-1-ylmethylphenyl]-isobutyramide (7) preferably, less than 1.0%, more preferably, 0.1% and most preferably, below quantitation limits.

NMR data of Anastrozole (1) and related substances (6) and (7)

| | $^1$H-NMR (DMSO-$d_6$) | $^{13}$C-NMR (DMSO-$d_6$) |
|---|---|---|
| Anastrozole | 8.72 (s, 1H), 8.01 (s, 1H), 7.57 (t, 1H, J = 1.6 Hz), 7.46 (d, 2H, J = 1.6 Hz), 5.51 (s, 2H) and 1.68 (s, 12H). | 151.9, 144.4, 142.7, 137.8, 124.4, 124.2, 121.6, 51.8, 36.8 and 28.2. |
| Related Substance (6) | 8.88 (s, 1H), 7.99 (s, 1H), 7.40 (s, 1H), 7.30 (s, 1H), 7.24 (s, 1H), 6.95 (d, 2H, J = 9.9 Hz), 5.43 (s, 2H), 1.65 (s, 6H) and 1.41 (s, 6H). | 177.4, 151.8, 147.5, 144.3, 141.6, 136.7, 125.0, 124.5, 122.7, 122.2, 52.1, 46.1, 36.7, 28.4 and 26.7. |
| Related Substance (7) | 8.61 (d, 1H, J = 6.9 Hz), 7.96 (d, 1H, J = 6.2 Hz), 7.28 (s, 1H), 7.14 (d, 2H, J = 1.4 Hz), 6.86 (d, 4H, J = 15.6 Hz), 5.38 (s, 2H) and 1.39 (s, 12H). | 179.6, 153.5, 148.3, 146.0, 137.4, 125.4, 124.9, 54.3, 47.9 and 28.8. |

Following the procedures as per Scheme—1 Anastrozole is obtained in its purer form but still some extent of the related substances 2-[3-(cyanodimethyl-methyl)-5-[1,2,4]triazol-1-ylmethyl-phenyl]-isobutyramide (6) and 2-[3-(1-carbamoyl-1-methylethyl)-5-[1,2,4]triazol-1-ylmethylphenyl]-isobutyramide (7) still remain contaminating Anastrozole, which is further purified using organic solvents preferably isopropanol, ethyl acetate or mixture of solvents preferably cyclohexane/ethyl acetate, cyclohexane/isopropanol or a mixture of solvents with water. Thus another embodiment of the present invention relates to the process for the preparation of Anastrozole free from related substances (6) and (7) by crystallization of crude Anastrozole using alcohols preferably selected from C1 to C10 alcohols and hydrocarbons, preferably selected from aliphatic hydrocarbons preferably C1 to C10.

EXAMPLE—1

2,2'-[5-(1H-1,2,4-Triazol-1-ylmethyl)-1,3-phenylene]di(2-methylpropiononitrile)(1), Anastrozole 4-Amino-1-[3,5-bis-(1-cyano-1-methylethyl)benzyl]-1H-[1,2,4]triazolium bromide (5) (70 g) was dissolved in cone. HCl (280 mL) in a 5 L R.B. flask and cooled to −5° C. A solution of sodium nitrite (15 g) in water (70 mL) was slowly added to the reaction mixture at 0-5° C. in 4 hrs and the reaction mixture was stirred for one hour at 0-5° C. and further at 10-20° C. for next 3 hours. The reaction mixture was quenched by the addition of a solution of urea (4.5 g) in water (15 mL). Toluene (700 mL) was added to the reaction mixture and the heterogeneous solution was further cooled down to 0-5° C. The solution was basified by the addition of liquor ammonia (365 mL) slowly in 4 hours at 5-25° C. Organic layer was separated and further washed with water (200 mL). Aqueous layer was removed and a solution of cone. HCl (140 mL) in water (140 mL) was added to the organic layer slowly in 30 minutes at 25-30° C. and reaction mass was heated at 60-65° C. for 30 minutes. The lower aqueous layer (280-300 mL), containing product was collected in a conical flask maintaining at 50° C. The aqueous part was again washed with toluene (700 mL) at 60-65° C. for 30 minutes. The lower aqueous layer, containing product was charged in a separating funnel and again washed with fresh toluene (700 mL). The aqueous layer, containing product was transferred in a R.B. flask and ethyl acetate (350 mL) was added to it. The heterogeneous solution was cooled to 0-5° C. basified by the slow addition of liquor ammonia (280 mL) in 2-3 hours at 5-25° C.

The solution was stirred for one hour at 25-35° C., and the upper organic layer (360-375 mL), containing product was separated and filtered through hyflow super cell bed. Solvent was distilled out below 50° C. under vacuum leaving approximately 100 mL ethyl acetate in the flask. The content of the flask was cooled down to 25-35° C. and cyclohexane (500 mL) was added to the solution slowly in 30 minutes. The precipitated solid product was filtered and washed with fresh cyclohexane (20 mL×2). The product was dried at 45-50° C. to get crude Anastrozole (44 g) with more than 98% HPLC purity contaminated with related substance (6) as 0.36% and with related substance (7) as 0.05%.

EXAMPLE—2

Removal of Related Substances (6) and (7) from Anastrozole

Anastrozole (33 g) from example—2 was dissolved in isopropanol (100 mL) at 45-50° C. The solution was cooled down to 25-35° C. and cyclohexane (100 mL) was added drop wise in 30 minutes. The solution was stirred at 25-35° C. for 2 hours; the precipitated solid product was filtered and washed with fresh cyclohexane (30 mL×2) and dried at 50° C. to get 23 g of pure Anastrozole contaminated with related substance (6) as 0.09% and with related substance (7) below detection limit.

EXAMPLE—3

Purification of Anastrozole

Pure Anastrozole (11 g) from Example—2 was further purified by dissolving in isopropanol (33 mL) at 45-50° C. The solution was cooled down to 25-35° C. and cyclohexane (33 mL) was added drop wise in 30 minutes. The solution was stirred at 25-35° C. for 2 hours; the precipitated solid product was filtered and washed with fresh cyclohexane (30 mL×2) and dried at 50° C. to get 8.9 g of pure Anastrozole containing with 0.03% of (6) as related substance and another related substance (7) below detection limit. Related substance (6) can be further removed below detection limit by repeating the same process.

We claim:

1. A process for the removal of compounds of the formula (6) and (7)

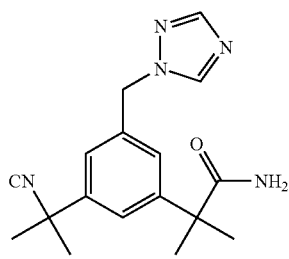

(6)

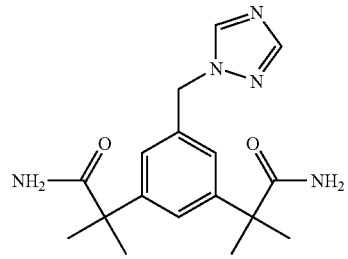

(7)

from Anastrozole, the process comprising:
  a. dissolving the Anastrozole containing the compounds of the formula (6) and (7) in an alcoholic solvent to form an alcoholic solution;
  b. adding a hydrocarbon to the alcoholic solution to form a hydrocarbon and alcoholic solution mixture; and
  c. precipitating the hydrocarbon and alcoholic solution mixture to form a solid product and isolating purified Anastrozole with compounds of the formula (6) and (7) removed therefrom.

2. The process as claimed in claim 1 wherein the alcoholic solvent in which the Anastrozole is dissolved is selected from a group consisting of $C_1$-$C_6$ alcohols.

3. The process as claimed in claim 1, wherein the hydrocarbons added to the alcoholic solution are anti-solvent and are selected from a group consisting of aromatic hydrocarbons, and aliphatic hydrocarbons.

4. The process as claimed in claim 3, wherein the hydrocarbons are selected from a group consisting of $C_1$-$C_{10}$ hydrocarbons.

5. The process for the removal of compounds of the formula (6) and (7) from Anastrozole

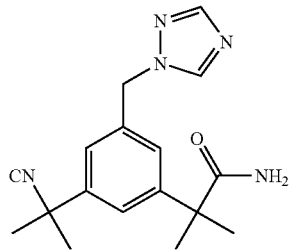

(6)

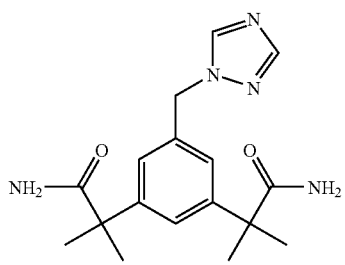

(7)

as claimed in claim 1, wherein the total amount of compounds of structures (6) & (7), after isolation, in less than 0.1%.

6. The process for the removal of compounds of the formula (6) and (7) from Anastrozole

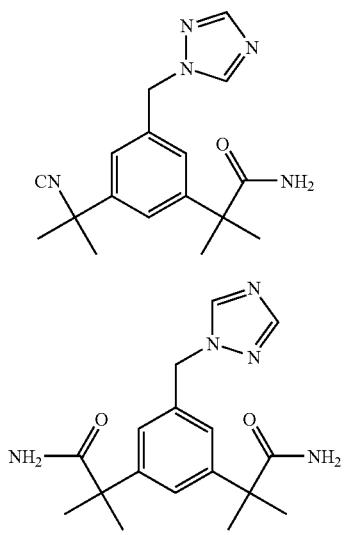

(6)

(7)

as claimed in claim 2, wherein the total amount of the compounds of structures (6) & (7), after isolation, is less than 0.1%.

7. The process for the removal of compounds of the formula (6) and (7) from Anastrozole

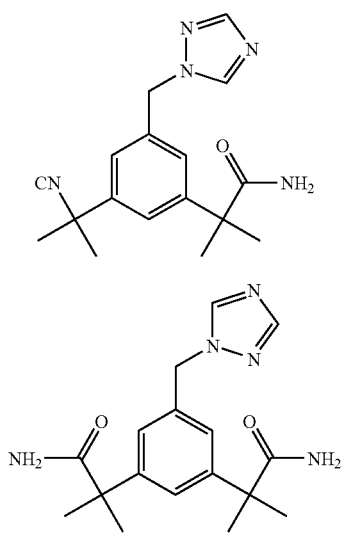

(6)

(7)

as claimed in claim 3, wherein the total amount of the compounds of structures (6) & (7), after isolation, is less than 0.1%.

8. The process for the removal of compounds of the formula (6) and (7) from Anastrozole

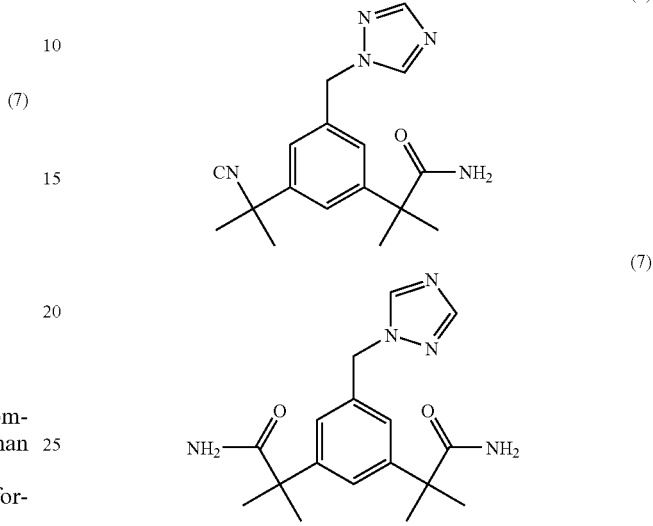

(6)

(7)

as claimed in claim 4, wherein the total amount of the compounds of structures (6) & (7), after isolation, is less than 0.1%.

9. The process as claimed in claim 1 wherein the alcoholic solvent in which the Anastrozole is dissolved is isopropole.

10. The process as claimed in claim 1 wherein the hydrocarbon used to precipitate out the purified Anastrozole is cylcohexane.

11. The process as claimed in claim 1 further comprising cooling the alcoholic solution before the step of adding the hydrocarbon to the alcoholic solution.

12. The process as claimed in claim 1 further comprising stirring the hydrocarbon and alcoholic solution mixture to form a precipitated solid product.

13. The process as claimed in claim 1 wherein precipitating the hydrocarbon and alcoholic solution mixture to form a solid product and isolating the purified Anastrozole with compounds of the formula (6) and (7) removed therefrom comprises filtering and washing the solid product with a hydrocarbon and drying the solid product.

\* \* \* \* \*